United States Patent
Tundidor Cabado et al.

(10) Patent No.: US 11,718,676 B2
(45) Date of Patent: Aug. 8, 2023

(54) ANTIBODIES WITH INCREASED AFFINITY FOR THE EPIDERMAL GROWTH FACTOR RECEPTOR AND FRAGMENTS DERIVED THEREFROM

(71) Applicant: CENTRO DE INMUMOLOGIA MOLECULAR, Havana (CU)

(72) Inventors: Yaima Tundidor Cabado, Havana (CU); Gertrudis Rojas Dorantes, Havana (CU); Kalet Leon Monzon, Havana (CU)

(73) Assignee: CENTRO DE INMUMOLOGIA MOLECULAR, Havana (CU)

( * ) Notice: Subject to any disclaimer, the term of this patent is extended or adjusted under 35 U.S.C. 154(b) by 337 days.

(21) Appl. No.: 16/767,356

(22) PCT Filed: Nov. 20, 2018

(86) PCT No.: PCT/CU2018/050004
§ 371 (c)(1),
(2) Date: May 27, 2020

(87) PCT Pub. No.: WO2019/105492
PCT Pub. Date: Jun. 6, 2019

(65) Prior Publication Data
US 2021/0002375 A1  Jan. 7, 2021

(30) Foreign Application Priority Data
Nov. 28, 2017 (CU) .................................. 2017-0148

(51) Int. Cl.
*C07K 16/28* (2006.01)

(52) U.S. Cl.
CPC ...... *C07K 16/2863* (2013.01); *C07K 2317/24* (2013.01); *C07K 2317/54* (2013.01); *C07K 2317/565* (2013.01); *C07K 2317/567* (2013.01); *C07K 2317/569* (2013.01)

(58) Field of Classification Search
CPC ............ C07K 16/2863; C07K 2317/24; C07K 2317/54; C07K 2317/565; C07K 2317/567; C07K 2317/569; A61K 2039/505
See application file for complete search history.

(56) References Cited

U.S. PATENT DOCUMENTS 5,891,996 A    4/1999   Mateo de Acosta del Rio et al.

OTHER PUBLICATIONS

Janice M. Reichert, "Marketed Therapeutic Antibodies Compendium" MABS, vol. 4, No. 3, 413-415 (2012).
Wark et al., "Latest Technologies for the Enhancement of Antibody Affinity" Advanced Drug Delivery Reviews, vol. 58, No. 5-6, 657-670 (2006).
Kim et al., "Affinity Maturation of Monoclonal Antibodies by Multi-Site-Directed Mutagenesis", Monoclonal Antibodies Methods and Protocols, Methods in Molecular Biology, 407-420 (2014).
Holger Thie, "Affiniy Maturation by Random Mutagenesis and Phase Display", Antibody Engineering, vol. 1, 397-409 (2010).
Almagro et al.,Antibody Engineering: Humanization, Affinity Maturation, and Selection Techniques, Therapeutic Monoclonal Antibodies: From Bench to Clinic, 311-334 (2009).
Renaut et al., "Affinity Maturation of Antibodies: Optimized Methods to Generate High-Quality ScFv Libraries and Isolate IgG Candidates by High-Throughput Screening", Methods in Molecular Bio, vol. 24, 1, 451-461 (2007).
Brockmann et al., "Synthetic Single-Framework Antibody Library Integrated with Rapid Affinity Maturation by VL Shuffling", Protein Engineering, Design and Selection, vol. 24, No. 9, 691-700 (2011).
International Search Report for corresponding Int'l Patent Appl. No. PCT/CU2018/050004, pp. 1-8 (2019).

*Primary Examiner* — Ruixiang Li
(74) *Attorney, Agent, or Firm* — Hoffman and Baron, LLP

(57) ABSTRACT

This invention provides new antibodies (Ab) and fragments that recognize the extracellular region of the human epidermal growth factor receptor (hEGFR) with a higher affinity than the Ab nimotuzumab, thus been able to recognize more efficiently lines with medium expression of EGFR. The present invention also relates to pharmaceutical compositions comprising as active principle the disclosed Abs and fragments and their use in the therapy of tumors with EGFR expression. In addition, it relates to the use of the Abs and fragments disclosed linked to a radioisotope or fluorophore for the localization of EGFR positive tumors. Additionally, the Abs and fragments disclosed can be used in the directionalization of the immune response to EGFR positive tumor cells when they are fused to protein or protein domains of immunological interest.

11 Claims, 6 Drawing Sheets
Specification includes a Sequence Listing.

FIGURE 3

|  | CDR1 | CDR2 | CDR3 |  |
|---|---|---|---|---|
| FabR3 original | GYTFTNYYIY | GGINPTSGGSNFNEKFKT | TRQGLWFDSDGRGF |  |
| 3AS22 | ---------- | ------NNQQ-H------ | -------------- | (6) |
| 3AS9 | ---------- | -------QQNH------- | -------------- | (3) |
| 3AS8 | ---------- | -------LR-QAV----- | -------------- | (7) |
| 3AS30 | ---------- | ------VTQRPV------ | -------------- | (3) |
| 3AS6 | ---------- | -------THAQA------ | -------------- | (4) |
| 3AS32 | ---------- | -----------I------ | -------------- | (1) |
| 3AS4 | -----D---- | -------T---------- | -------------- | (3) |
| 3AS3 | -----D---- | ------------------ | -------------- | (1) |
| 3AS21 | --N--D---- | ---------------H-- | -------------- | (1) |
| 3AS14 | --P-S----- | -----------V------ | -------------- | (1) |
| 3AS31 | --P------- | -----------V------ | -------------- | (1) |

|  | CDR1 | CDR2 | CDR3 | A |
|---|---|---|---|---|
| FabR3 original | GYTFTNYYIY | GGINPTSGGSNFNEKFKT | TRQGLWFDSDGRGF | |
| 3AS4+22 | ------D---- | ------NNQQ-H------ | -------------- | |
| 3AS4+30 | ------D---- | ------VTQRPV------ | -------------- | |

ANTIBODIES WITH INCREASED AFFINITY FOR THE EPIDERMAL GROWTH FACTOR RECEPTOR AND FRAGMENTS DERIVED THEREFROM

CROSS-REFERENCE TO RELATED APPLICATIONS

This application is a National Stage Application that claims a benefit of priority from Application No. PCT/CU2018/050004 filed Nov. 20, 2018, which claims priority to Application No. CU 2017-0148, filed Nov. 28, 2017, the disclosures of which are herein incorporated in their entirety.

SCOPE OF THE TECHNIQUE

The present invention relates to the fields of Biotechnology and Medicine, particularly to variants of the monoclonal antibody (mAb) nimotuzumab and antigen-binding fragments derived therefrom which have mutations in the CDR1 and CDR2 of the variable region of the heavy chain and recognize the extracellular region of the human epidermal growth factor receptor (hEGFR) with greater affinity, as well as its diagnostic and therapeutic application.

BACKGROUND

EGFR is a transmembrane glycoprotein, which has an extracellular ligand binding region, and an intracellular region with tyrosine kinase activity. These ligands include: the epidermal growth factor (EGF), amphiregulin, the transforming growth factor-α, betacellulin, epiregulin, and the heparin-binding EGF. (Olayioye, M. y et al., The EMBO Journal, 19: 3159-3167, 2000; Yarden, Y. and Sliwkowski, M., Nature Reviews, 2: 127-137, 2001). The binding of the ligands to the receptor induces conformational changes and arrangements in the extracellular region that cause receptor dimerization and activation (Ogiso, H. et al., Cell 110: 775-787, 2002). This receptor is involved in different cellular processes that contribute to the maintenance and survival of epithelial cells. However, deregulation of the EGFR/EGF pathway by overexpression or constitutive activation promotes the proliferation of tumor cells, invasion, and is associated with poor prognosis in many malignancies (Yarden, Y. and Sliwkowski, M., Nature Reviews. 2: 127-137, 2001). For this reason, EGFR is considered a tumor-associated antigen (Ag) very important for the development of antitumor therapies.

There are three anti-EGFR mAbs currently marketed: cetuximab (Erbitux), panitumumab (Vectibix), and nimotuzumab (TheraCIM) (Reichert, J., MAbs. 4: 413-415, 2012) and seven others are in the phases I-III of clinical trials (Reichert, J. and Dhimolea, E., Drug Discovery Today, 17: 954-963, 2012). They were specifically designed to recognize the extracellular region of EGFR, competitively inhibit ligands binding and receptor dimerization, and thus inhibit receptor auto-phosphorylation and the signaling cascade that leads to its activation (Burgess, A. and others, Molecular Cell, 12: 541-552, 2003). Nimotuzumab (mAb R3) is a humanized mAb of IgG1 isotype that recognizes hEGFR obtained by cloning the DNA of the hypervariable regions of ior egf/r3 murine mAb and the human frameworks of the variable and constant regions of the heavy and light chains (REI y NEWN respectively) (Mateo, C. et al., Immunotechnology 3: 71-81, 1997). R3 mAb recognizes the EGFR with similar affinity and has the same capability to inhibit the EGF binding to the receptor than its murine predecessor. This variant is less immunogenic than the chimeric version of mAb ior egf/r3 (Mateo, C. et al., Immunotechnology 3: 71-81, 1997). Nimotuzumab recognizes an epitope in domain III of the extracellular region of EGFR that overlaps with the binding site of the ligands in this domain, which explains its ability to block ligand binding and subsequent receptor activation (Tundidor, Y. et al., mAbs 6: 1013-1025, 2014). The efficacy of nimotuzumab has been demonstrated in clinical trials, in patients with head and neck tumor (Crombet, T. et al., J Clin Oncol 22: 1646-1654, 2004), glioma (Ramos, T. et al., Cancer Biol. Ther. 5: 375-379, 2006; MacDonald, T. et al., Neuro Oncol., 13: 1049-1058, 2011) and esophageal tumor (Ramos-Suzarte, M. et al., Cancer Biology & Therapy 13: 600-605, 2012). This antibody (Ab) is in phase III clinical trials for nasopharyngeal cancer, locally advanced esophageal cancer and esophageal squamous cell carcinoma (Galluzzi, L. et al., OncoImmunology, 1:28-37, 2012).

Unlike other Abs directed against EGFR, both in preclinical studies in green monkeys *Cercopithecus aethiops sabaeus* (Arteaga, M. and others, Cancer Biology & Therapy. 6: 1390-1395, 2007) and in clinical studies (Crombet, T. et al., J Clin Oncol 22: 1646-1654, 2004; Ramos, T. et al., Cancer Biol Ther 5: 375-379, 2006; Ramos-Suzarte, M. et al., Cancer Biology & Therapy 13: 600-605, 2012; Strumberg, D. et al., Invest New Drugs, 30: 1138-1143, 2010), with nimotuzumab no signs of severe toxicity usually associated with drugs directed against this Ag has been detected. These evidences suggest that nimotuzumab is the only anti-EGFR agent that can be used chronically (Allan, D., The Oncologist, 10: 760-761, 2005). The low toxicity profile, but with antitumor effect, of this mAb could be due to its intermediate affinity (10-8) (Crombet, T. et al., J Clin Oncol 22: 1646-1654, 2004). The authors predict that mAbs with intermediate affinity should have high antitumor effect and low toxicity since tumor uptake (high expression of EGFR) is favored over uptake in normal tissue (low expression of EGFR). On the other hand, high affinity mAbs (such as cetuximab) would be captured by both tumor and normal cells; and low affinity mAbs would have little effect because of low incorporation into tumors (Crombet, T. et al., J Clin Oncol 22: 1646-1654, 2004). However, it has been described that the antitumor effect of nimotuzumab depends on the expression of EGFR, since its efficacy is reduced in tumors with medium or low expression of this receptor (Akashi, Y. et al., British Journal of Cancer, 98: 749-755, 2008). Therefore, obtaining a variant of nimotuzumab with a moderate increase in its affinity for the receptor could translate into an antibody (Ab) with greater antitumor effect but that maintains at the same time its low toxicity. Obtaining this intermediate affinity variant from nimotuzumab, and maintaining its fine epitopic specificity (which is unique among therapeutic Abs against EGFR), (Tundidor, Y. et al., mAbs 6: 1013-1025, 2014), would contribute to conserve the valuable properties of the original antibody.

The affinity maturation of the Abs is a process that occurs naturally; however with the development of the combinatorial biology, this phenomenon has been reproduced in the laboratory. These technologies of directed evolution require different steps: mutation, display, selection and amplification (Wark, K. and Hudson, P., Advanced Drug Delivery Reviews, 58: 657-670, 2006). The phage display technology provides a powerful platform for the generation of new human Abs and for improving its affinity in vitro (Hoogenboom, H., Nat Biotechnol, 23: 1105-1116, 2005).

The inventors of the present invention found phage displayed-mutated variants of nimotuzumab, with an increased binding capacity to the extracellular region of hEGFR. The set of mutations that possess these variants has not been previously described nor is it predictable from the analysis of the crystal structure of the antigen-binding fragment (Fab) of nimotuzumab. Therefore, the novelty of this invention consists in providing new fragments and mAbs that recognize hEGFR with a higher affinity (3 to 4 times higher), so they can recognize lines with medium expression of EGFR more efficiently than nimotuzumab. Likewise, these mAbs showed a greater ability to inhibit ligand-mediated EGFR phosphorylation as compared with nimotuzumab, which indicates that they have a greater antitumor effect than nimotuzumab. All of the above allows supports the use of these fragments and mAbs in the diagnosis or therapy of tumors with intermediate expression of EGFR.

BRIEF DESCRIPTION OF THE INVENTION

The present invention relates to recombinant mAbs that recognize the extracellular region of the Her1 hEGFR and that have more than 95% identity with respect to nimotuzumab antibody.

In one embodiment it refers to mAbs where the sequences of the complementary determining region (CDR) of the CDR2 of the variable region of the heavy chains are selected from the group comprising:
SEQ ID NO. 20 and
SEQ ID NO. 21
the sequences of CDR1 and CDR3 of the heavy chains are SEQ ID NO. 9 and SEQ ID NO. 3 respectively and the CDR sequences of the variable region of the light chains are:
CDR 1 SEQ ID NO. 22
CDR 2 SEQ ID NO. 23
CDR 3 SEQ ID NO. 24.

In another embodiment, the recombinant mAbs of the present invention are characterized in that the sequence of the CDR2 of the variable region of the heavy chains is selected from the group comprising:
SEQ ID NO. 10,
SEQ ID NO. 11,
SEQ ID NO. 12,
SEQ ID NO. 17,
SEQ ID NO. 18 and
SEQ ID NO. 29,
the sequence of the CDR1 is SEQ ID NO. 9 and the sequence of CDR3 is SEQ ID NO. 3 in said heavy chains and the sequences of the CDRs of the variable region of the light chains are:
CDR 1 SEQ ID NO. 22
CDR 2 SEQ ID NO. 23
CDR 3 SEQ ID NO. 24.

Another embodiment of the present invention relates to mAbs where the CDR2 sequence of the variable region of the heavy chains is selected from the group comprising:
SEQ ID NO. 2 and
SEQ ID NO. 8,
the sequences of the CDR1 and CDR3 of the heavy chains are SEQ ID NO. 1 and SEQ ID NO.3 respectively and the CDR sequences of the variable region of the light chains are:
CDR 1 SEQ ID NO. 22
CDR 2 SEQ ID NO. 23
CDR 3 SEQ ID NO. 24.

In a further embodiment the mAbs of the present invention are characterized in that the CDR1 sequence of the variable region of the heavy chains is selected from the group comprising:
SEQ ID NO. 13 and
SEQ ID NO. 19,
the CDR2 and CDR3 sequences of the heavy chains is SEQ ID NO. 14 and SEQ ID NO. 3 respectively and the CDR sequences of the variable region of the light chains are:
CDR 1 SEQ ID NO. 22
CDR 2 SEQ ID NO. 23
CDR 3 SEQ ID NO. 24.

Particularly, the present invention relates to a mAb characterized by having the following variable region sequence of the heavy and light chains:
Heavy chain
CDR1 SEQ ID NO. 15
CDR2 SEQ ID NO. 16
CDR3 SEQ ID NO. 3
Light chain
CDR 1 SEQ ID NO. 22
CDR 2 SEQ ID NO. 23
CDR 3 SEQ ID NO. 24.

The present invention encompasses all previous mAbs where the framework regions (FW) of the variable region of the heavy and light chains have the following sequences:
Heavy chain
FW 1 SEQ ID NO. 4
FW 2 SEQ ID NO. 5
FW 3 SEQ ID NO. 6
FW 4 SEQ ID NO. 7
Light chain
FW 1 SEQ ID NO. 25
FW 2 SEQ ID NO. 26
FW 3 SEQ ID NO. 27
FW 4 SEQ ID NO. 28

Additionally, the disclosed Abs comprise the human IgG1 constant regions to heavy chain and human kappa to light chain.

In a particular embodiment it refers to the fragments derived from the previous Abs where said fragments can be of Fab type, (Fab)2 and single-chain variable region fragments. In another embodiment, the present invention relates to a pharmaceutical composition useful in cancer therapy that has as active principle the mAbs or fragments disclosed in a range from 50 to 400 mg and a pharmaceutically acceptable carrier. Additionally, it is related to a pharmaceutical composition useful in the diagnosis of tumors whose active principle are mAbs or fragments disclosed in a range from 1 to 9 mg and a pharmaceutically acceptable vehicle.

In another embodiment, the present invention relates to the use of mAbs and fragments disclosed in the therapy of tumors that express EGFR; as well as in the diagnosis of tumors bearing EGFR, when they are conjugated to an appropriate marker. It is also related to the use of these mAbs and fragments to direct the immune response against EGFR positive tumors, when they are conjugated with proteins or protein domains of immunological interest.

DETAILED DESCRIPTION OF THE INVENTION

Obtaining Fragments Derived from Nimotuzumab with Increased Binding Capacity to the Extracellular Region of Human EGFR The present invention relates to 13 fragments derived from nimotuzumab that share more than 97% identity with the amino acid sequence thereof and have increased ability to bind to the extracellular region of hEGFR. Mutations of the variants described in the present invention lead to obtaining variants of nimotuzumab with the ability to recognize a greater number of human cells with a medium expression of EGFR as compared with the original Fab of nimotuzumab.

The fragments described in the present invention can be obtained by selecting mutated variants of the Fab of nimotuzumab due to their ability to bind to the extracellular region of hEGFR, from libraries of more than $10^7$ filamentous phage-displayed molecules. The genes corresponding to these variants can be inserted into a phagemid type expression vectors (fused to one of the genes encoding the capsid proteins of the filamentous phage) and used for the production of viral particles that expose on their surface the proteins variants. The starting libraries can include different degrees of diversification in a set of positions of the complementary determining regions (CDRs), which would allow for a thorough exploration of this region, which is functionally important for the Ag-Ab interaction. Each of the original residues in these positions can be replaced by a mixture of the 20 amino acids, by a pre-defined set of residues that share some physical-chemical property (ies) such as hydrophobicity, aromatic character, net charge and/or size, or be subjected to soft randomization by introducing a minority proportion of a random mixture of nucleotides at each corresponding codon position (which would maintain a predominance of the original sequence). The chosen positions can be diversified simultaneously in the same library, or in several separate libraries. These libraries can contain variable proportions of molecules with one or several mutations, conservative or not, with respect to the original nimotuzumab Fab.

Selection of Analog Fragments and Mabs of Nimotuzumab with Increased Binding Capacity to the Extracellular Region of hEGFR The selection of phages that have variants with increased binding capacity to the extracellular region of hEGFR can be based on the incubation of the phage mixtures from the libraries in contact with the hEGFR Ag immobilized on a solid surface, the removal of non-bound phages by washing, and the elution of bound phages under conditions that interfere with protein interactions. Several successive cycles of selection can be performing under similar conditions. The analysis of the DNA sequences inserted in the selected phagemids may reveal regularities that lead to the identification of the most abundant substitution that would be related to the increase of the EGFR binding capacity. The recurrent mutations found, whether they are individual modifications or combinations of changes selected directly from the libraries, can be combined with among themselves to form new variants and obtain additional increases in EGFR binding capacity.

The binding capacity to the hEGFR of each of the variants selected directly from the libraries, or designed and constructed later, can be evaluated by immunochemical techniques taking advantage of the phage display format that allows the simultaneous characterization of multiple variants.

Alternatively, the fragments of the present invention can be obtained by exploiting other platforms of combinatorial biology, such as ribosomes or yeasts display.

Additionally, the genes that encode the new variable regions can be cloned into expression vectors of mammalian cells and produce the recombinants mAbs containing the new mutations. It can also be verified that in this format, the mAbs obtained retain the ability to preferentially recognize the extracellular region of hEGFR as compared to nimotuzumab, through affinity measurements based on surface plasmon resonance (BIAcore).

Demonstration of the Functional Superiority of the New mAbs and Fragments Derived from Nimotuzumab Functional superiority of each of the fragment variants selected directly from the libraries or subsequently constructed in fragments or complete Abs formats, can be demonstrated in in vitro or in vivo assays. To each variant, the recognition of cell lines with different expression of EGFR can be evaluated by flow cytometry, verifying that the new variants recognize a higher percentage of positive cells and with a higher fluorescence mean intensity; and this effect is more evident in lines with medium or low EGFR expression. To this purpose, cells with the following characteristics will be used:

- high expression of EGFR: such as A431 squamous cell carcinoma of human origin, MDA-MB-468 breast adenocarcinoma with pleural fluid metastasis of human origin, without being limited to these one
- medium expression of EGFR: H125 and H292 lung adenocarcinoma of human origin, without being limited to these one.
- low expression of EGFR: U1906 small cell lung cancer of human origin, MDA-MB-231 breast adenocarcinoma of human origin, SKOV3 ovarian carcinoma, SKBR3 breast cancer, without being limited to these one.

The ability of each mAb or fragment to inhibit the phosphorylation of EGFR mediated by its ligand (EGF) can also be evaluated, at different concentrations and in cell lines with different expression of EGFR. Proliferation inhibition assays by Alamar blue can also be performed on lines with different receptor expression. Additionally, the ability of each mAb to induce Ab-dependent cellular cytotoxicity can be determined in lines with different expression of the receptor. In all cases it could be expected that the higher affinity variants show a greater effect and that it would be more evident in lines with medium or low EGFR expression.

On the other hand, the anti-tumor effect of mAbs or fragments in athymic mice bearing human tumors with different expression of EGFR could be measured, where the delay in tumor growth would be measured.

Additionally, the fragments or mAbs with radioactive isotopes or with fluorophores can be labeled and inoculated in athymic mice bearing human tumors with different EGFR expression. This allows for the evaluation of the ability of the fragments to detect in vivo the recognition of tumors, which supports their use as tools for the diagnosis of cancer by obtaining images.

Therapeutic Application and Methods of Treatment of New mAbs and Derived Fragments The new mAbs and fragments obtained in the present invention have higher affinity than nimotuzumab, which allows for their use them in scenarios where nimotuzumab has limitations, such as in cells with low or intermediate expression of EGFR. Said mAbs may be used in the treatment of patients with head and neck tumors, glioma, esophagus, lung and pancreas.

For therapeutic use, the mAbs and fragments must be administered to a subject carrying the disease either independently or combined with conventional therapies for the treatment of cancer such as radiotherapy or chemotherapy, to enhance their therapeutic action. The route of administration may be any of those described in the state of the art for the parenteral administration of drugs, preferably by intravenous or subcutaneous route.

To obtain the desired therapeutic effect, the mAbs and fragments of the present invention should be administered in doses that are in the range of concentrations for which they produce an antitumor effect without toxic manifestations. The ranges of doses to be explored can vary from 50 mg to 400 mg per patient in 6 weekly cycles of treatment. Treatment with the new variants with higher affinity could be adjusted to administer lower doses and maintain an effect similar to that of nimotuzumab or the recommended dose for nimotuzumab (200 mg) could be used, showing a greater antitumor effect, which would depend on the toxicity profile of the new mAbs and fragments.

The mAbs and fragments of the present invention may have application for the diagnosis of EGFR positive tumors by conjugating them with radioisotopes or fluorophores; since they have greater affinity and ability to recognize cells with medium or low expression of EGFR, which is an advantage as compared to nimotuzumab in the diagnosis of tumors with this feature.

To use them as detection tools these mAbs and fragments would be administered in patients that bear tumors to identify by means of imaging the location of the tumor or possible EGFR positive metastases. The mAbs and fragments conjugated to radioisotopes or fluorophores should be administered in doses in the range of concentrations for which the kinetics of distribution in the tissues and their elimination make it possible to obtain fast quality images. This range can be from 0.5 mg to 9 mg per patient, preferably 3 mg.

Additionally, the fragments described in the present invention can be fused to proteins or protein domains of immunological interest, with the aim of directing the immune response to the EGFR positive tumor cells. This application has the advantage of combining the potentiality of both therapies separately by concentrating the response in the tumor site; Fab fragments provide specificity for tumor cells that express the Ag, while proteins or fused protein domains play their immunological role, which could have a superior effect to monotherapies.

Pharmaceutical Compositions

The mAbs and fragments described in the present invention are administered as part of a pharmaceutical composition useful in cancer therapy. Preferably, the present invention encompasses pharmaceutical compositions, comprising a pharmaceutically acceptable carrier. Pharmaceutically acceptable carriers include, but are not limited to: saline solution, phosphate buffered saline, and similar. Other buffering agents, dispersing agents, and non-toxic inert substances suitable for administration to a patient may be included in the compositions of the present invention. The compositions are normally sterile and free of undesirable particles.

The present invention is further elaborated with the following examples and drawings. However, these examples should not be construed as limiting the scope of the invention.

BRIEF DESCRIPTION OF THE FIGURES

FIG. 3. Alignment of the amino acid sequence of the three CDRs of the heavy chain variable region (VH) of nimotuzumab and of the 11 variants of the FabR3 with unique sequences after three rounds of selection of the library against the extracellular region of human EGFR. The dashes indicate that the original amino acid was maintained in that position. The number of times the sequence was repeated is indicated in parentheses.

EXAMPLES

Example 1: Successful M13 Filamentous Phage-Display of the Antigen-Binding Fragment of Nimotuzumab (FabR3)

Figure 1:
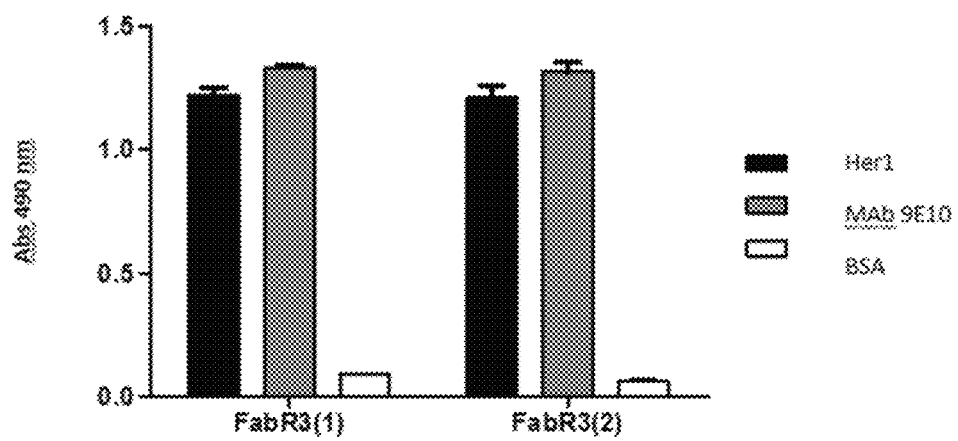
FIG. 1. Evaluation by ELISA of the recognition of filamentous phages displayed FabR3. The different preparations of purified phages were adjusted to a concentration equivalent to $10^{12}$ viral particles/ml. Absorbance was measured at 490 nm.

The genes encoding the variable regions of the light (VL) and heavy (VH) chains of nimotuzumab flanked by the ApaLI/XhoI and SfiI/BstEII restriction sites, respectively, were amplified by PCR. Both VL and VH gene fragments were cloned into pCES1 vector (Haard, H., Methods in Molecular Biology. 178: 87-100, 2002) followed by the genes coding for the kappa light constant region (CK) and the constant heavy region (CH1), respectively. The gene coding for the CH1 region is linked to a gene coding for the c-myc tag peptide and followed by the gene III. This genetic construct encoded an Ag binding fragment derived from nimotuzumab (FabR3). Competent bacterias of strain TG1 of the *Escherichia coli* species were transformed with the resulting genetic constructs and used to produce and purify phages-displaying FabR3 fused to the P3 protein of the viral capsid, at a scale of 50 mL (Marks, J. et al. J. Mol. Biol. 222: 581-597, 1991). The specific recognition of purified phages-displaying the molecules was evaluated by ELISA (FIG. 1).

To this end, polystyrene plates (MaxiSorp, USA) were coated with the Ag of nimotuzumab, the extracellular region of the human EGFR (Her1) (Ramirez, B. et al., Int. J. Cancer, 119: 2190-2199, 2006), the anti c-myc tag 9E10 mAb (Center of Genetic Engineering and Biotechnology of Sancti Spiritus, Cuba) and BSA as an unrelated molecule. The bound phages were detected with the anti-M13 mAb conjugated to horseradish peroxidase (GE Healthcare, USA) and the corresponding substrate of the enzyme. As shown in FIG. 1, FabR3 displayed on phages was properly folded, measured by 9E10 mAb recognition which detects the display levels and because it retained the ability of nimotuzumab to recognize Her1 specifically.

Example 2: Selection and Characterization of Filamentous Phages-Displaying Fragments of FabR3 Variants with Greater Reactivity for the Extracellular Region of Human EGFR A soft randomization strategy of 25 residues, located in protruding segments of the three CDRs (according to the AbM definition) of the heavy chain of nimotuzumab, was designed. Most of them (24/25) were replaced by a mixture that potentially contained all 20 amino acids, but that retained the original residue in most of the molecules of the library. To this end, degenerate codons that preserved the original nucleotide in 90% in each position were introduced, while the remaining 10% corresponded to an equimolar mixture of the other three nucleotides. The other residue (F29) was only replaced by other hydrophobic residues (I, L, M, V), although the original residue predominated in the majority of the molecules of the library. To do this, a degenerate codon was used in positions one and three of the triplet that maintained 90% of the original nucleotide (T and C respectively) while the remaining 10% corresponded to an equimolar mixture of the other three nucleotides, the second position of the triplet (T) was not modified. The designed library was constructed in a Fab format by cloning the variable regions in pCES-1 vector. In this way, a library of Nimotuzumab Fab variants composed of $1.5 \times 10^7$ members was built.

Figure 2:
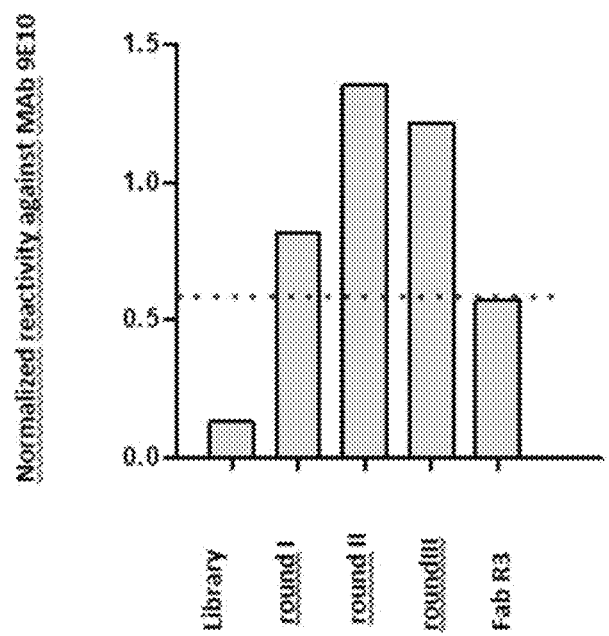
FIG. 2. Evaluation by ELISA of the reactivity of the phage mixture of the FabR3 library after three rounds of selection against the extracellular region of human EGFR. The different purified phage preparations were adjusted to a concentration equivalent to $10^{11}$ viral particles/ml. Absorbance was measured at 490 nm.

The phages produced from the library were purified by precipitation with polyethylene glycol according to previously established procedures (Marks, J. et al., J. Mol. Biol. 222: 581-597, 1991). To isolate functional phage-displayed mutated variants of FabR3 with greater capacity of binding to their antigen the viral particles were incubated on immunotubes (Nunc, Denmark), coated with Her1. After washing to remove the unbound phages, the bound phages were eluted by incubation with a basic solution of triethylamine. Bacteria of TG1 strain were infected with the selected phages, which were amplified with M13KO7 helper phage, and used as starting material for a new round of selection. Three rounds of phage selection were carried out and an increase in the reactivity by the Her1 of the phage mixture as the number of cycles increased was observed (FIG. 2). The sequencing of the genes inserted in the selected phagemid, which came from the third selection cycle, revealed 11 unique sequences divided into two groups (FIG. 3). The first group consisted of variants in which only the CDR2 was randomized and the second group where mutations in the CDR1 and CDR2 appeared.

Figure 4A:
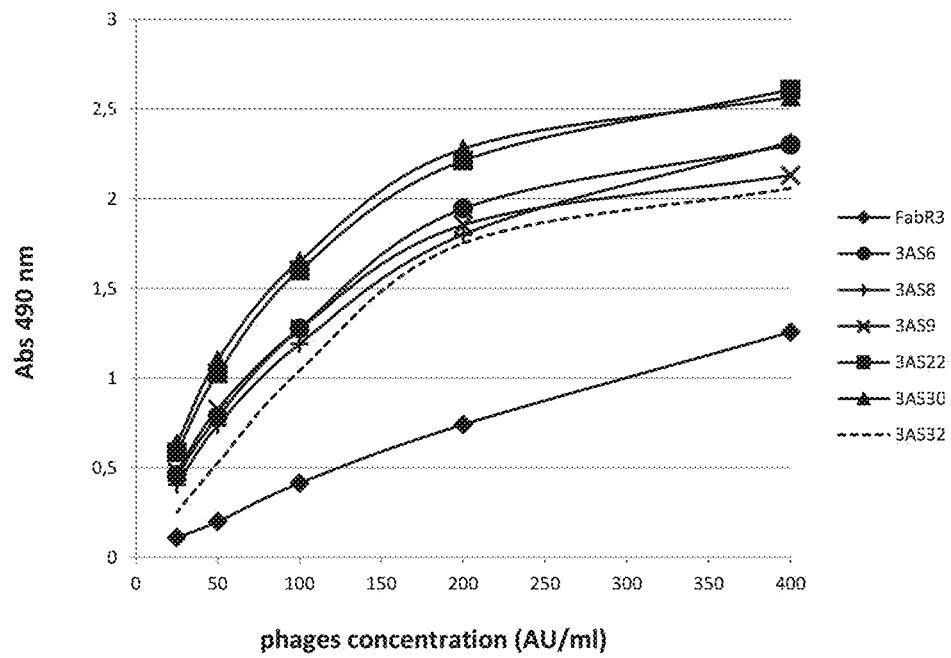
FIG. 4. Evaluation by ELISA of the recognition of phages-displayed FabR3 variants with unique sequences obtained from the soft randomization library after three rounds of selection against the extracellular region of human EGFR. The phage preparations were previously normalized according to the amounts of protein displayed. (A) Variants included in group 1, only have mutations in the CDR2 of the VH. (B) Variants of group 2, present mutations in the CDR1 and the CDR2 of VH. Absorbance was measured at 490 nm.
Figure 4B:
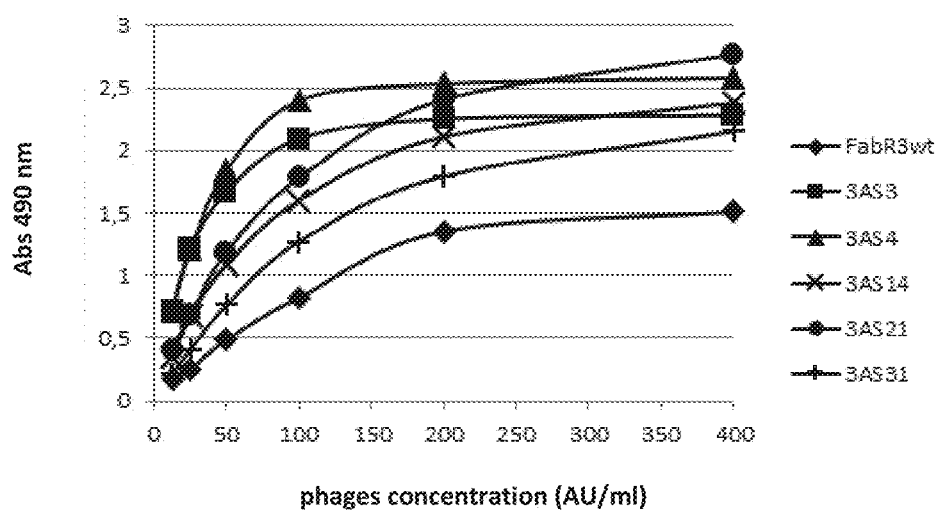
Figures 5A, 5B:
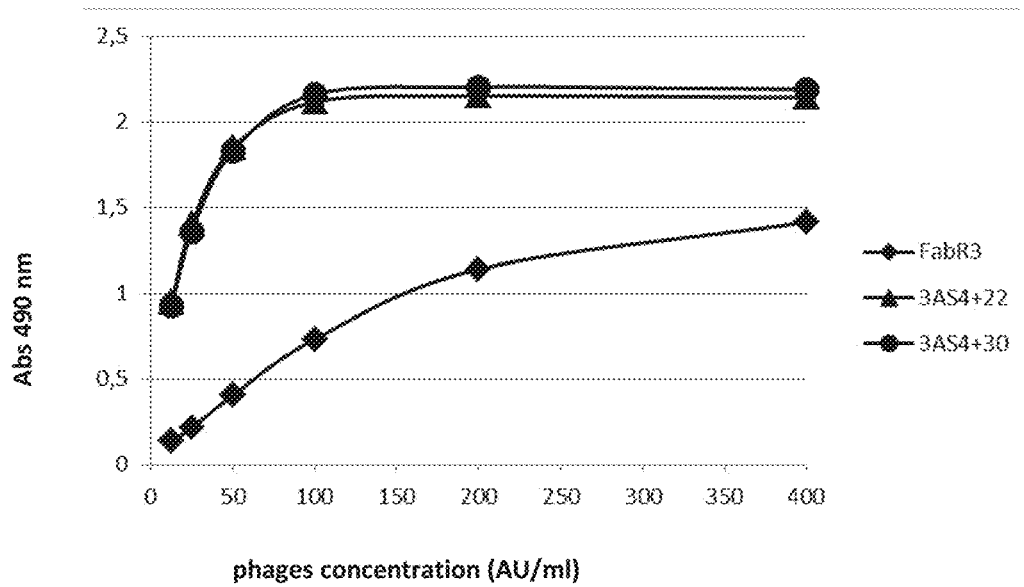
FIG. 5. Variants of FabR3 on phages constructed from the combination of the most recurrent CDR1 mutation and the CDR2 mutations of the best FabR3 variants of group 1. (A) Alignment of the amino acid sequence of the three CDRs of the VH of the original nimotuzumab and the two constructed variants. (B) Evaluation by ELISA of the recognition of the constructed variants. Absorbance was measured at 490 nm.

Example 3: Demonstration of the Increase of the Reactivity of the New Filamentous Phages-Displayed FabR3 Variants by the Extracellular Region of hEGFR Competent bacteria of the *E. coli* TG1 strain were transformed with the genetic constructs rescued after three selection rounds that contained unique sequences different from that of the original nimotuzumab. From these sequences, phages displaying FabR3 variants were produced and purified. To determine the reactivity of these new variants by Her1, the recognition of phage preparations at different concentrations of viral particles was determined by ELISA. All the variants evaluated, the 6 with mutations exclusively in the CDR2 (FIG. 4A), and the 5 with mutations in the CDR1 and CDR2 (FIG. 4B) showed greater reactivity toward Her1 than the original FabR3 at the different concentrations evaluated. Additionally, two new variants were constructed by Kunkel mutagenesis which combined the CDR2 mutations that increased reactivity the most, with the most recurrent mutation of the CDR1 (FIG. 5A). The recognition of these new variants was evaluated by ELISA. The combination of the mutations was compatible because both variants showed a greater reactivity to Her1 than the original phage-displayed FabR3 (FIG. 5B).

Example 4: Demonstration of Increased Affinity of the New Variants of Nimotuzumab Produced as Soluble Protein in Mammalian Cells The genes encoding the original VH of nimotuzumab (R3 mAb) and the VH of the two constructed variants of nimotuzumab with mutations in the CDR1 and CDR2, as described in Example 3 (FIG. 5A) and which were named K4 and K5, as well as the original kappa light chain variable region (VK) of nimotuzumab were cloned into the mammalian cells expression vectors pSV-gpt and pSV-hyg, respectively (Orlandi, R. et al., PNAS: 3833-3837, 1989). The vectors with the genes of interest were linearized with Pvu I enzyme and precipitated in the presence of ethanol. The DNA reconstituted in phosphate-buffered saline was used to electroporate NS0 cells. To obtain R3, K4 and K5 mAb producing-clones, 4 µg of the pSV-gpt vector with the corresponding VH (Table 1) and 8 µg of the pSV-hyg-VK vector of the original nimotuzumab were co-transfected. The procedure for obtaining stable clones was carried out with xanthine, hypoxanthine and mycophenolic acid as selection drugs. This methodology allowed to obtaining the three molecules of interest as Abs of IgG1 isotype and light chain kappa. The produced Abs were purified from the supernatant by protein A affinity chromatography.

TABLE 1

Description of the VH and VL genes used to co-transfect NS0 cells to produce the R3, K4 and K5 mAbs.

| | pSV-gpt-VH | pSV-hyg-Vk |
|---|---|---|
| R3 mAb | Original | Original |
| K4 mAb | Mutations 3AS4 + 3AS22 | Original |
| K5 mAb | Mutations 3AS4 + 3AS30 | Original |

To demonstrate that the mutations obtained on phages that in that format showed a greater reactivity toward Her1, caused the same effect in the complete Ab, it was decided to measure the affinity by Biacore. Firstly, the Fab derived from the R3, K4 and K5 mAbs were obtained by enzymatic digestion with papain and subsequent separation by protein A. As shown in Table 2, the new K4 and K5 mAb showed an increase in affinity of 3 and 3.6 times, respectively, with respect to mAb R3.

TABLE 2

Affinity increase of K4 and K5 mAb with respect to nimotuzumab.

|        | Ka (1/Ms)       | Kd (1/s)          | KD (M)            | Increase |
|--------|-----------------|-------------------|-------------------|----------|
| R3 mAb | $1.879 * 10^4$  | $12.483 * 10^{-4}$ | $6.643 * 10^{-8}$ | —        |
| K4 mAb | $2.743 * 10^4$  | $6.019 * 10^{-4}$  | $2.194 * 10^{-8}$ | 3X       |
| K5 mAb | $3.305 * 10^4$  | $6.098 * 10^{-4}$  | $1.845 * 10^{-8}$ | 3.6X     |

Figure 6:
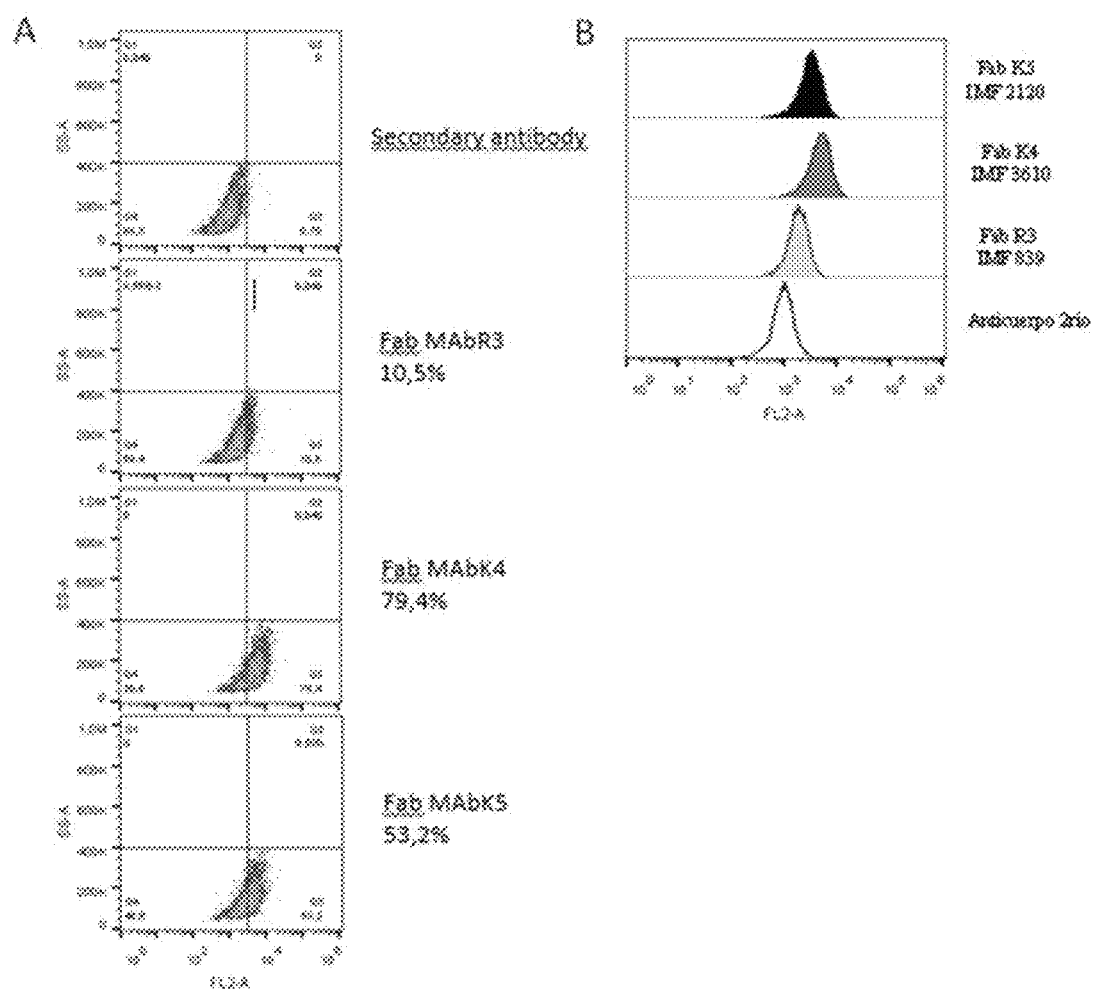
FIG. 6. Recognition of cells of the H125 line by the Fab derived from nimotuzumab, K4 and K5 mAbs. (A) Dot Plot graph showing the percentage of recognized EGFR positive cells. (B) Histograms of fluorescence mean intensity (EGFR positive cells).

Example 5: The Fab Derived from the K4 and K5 mAbs Produced in Mammalian Cells Showed Greater Recognition of H125 Lung Adenocarcinoma Human Cell Line than the Fab Derived from Nimotuzumab The ability of the Fabs derived from K4 and K5 mAbs to recognize the Her1 molecule was determined. In this case, the recognition of Her1 was evaluated by flow cytometry in a cell line, its natural context. To this end, the Fabs derived from R3, K4 and K5 mAbs were incubated at 1.25 µg/ml with H125 lung adenocarcinoma human cell line, which have a medium expression of the receptor. The Fabs bound to Her1 in the membrane of the cells were detected with a mouse anti-Human Kappa Light Chain mAb conjugated to phycoerythrin. As evidenced in FIG. 6A, the Fab derived from K4 and K5 mAbs recognized a higher percentage of Her1 positive cells and with higher fluorescence median intensity (FMI) (FIG. 6B) as compared to the Fab derived from R3 mAb.

Example 6: The Increase in Affinity of the K4 and K5 MAb Resulted in a Greater Capacity of these Abs to Inhibit the EGF-Mediated EGFR Phosphorylation To determine the capacity of the new mAbs to inhibit EGF-mediated phosphorylation, a Western Blot assay was performed. Two cell lines were used:

H125 lung adenocarcinoma human cell line (medium EGFR expression).

MDA-MB-468 breast adenocarcinoma with pleural fluid metastasis of human origin (high EGFR expression).

Figure 7:
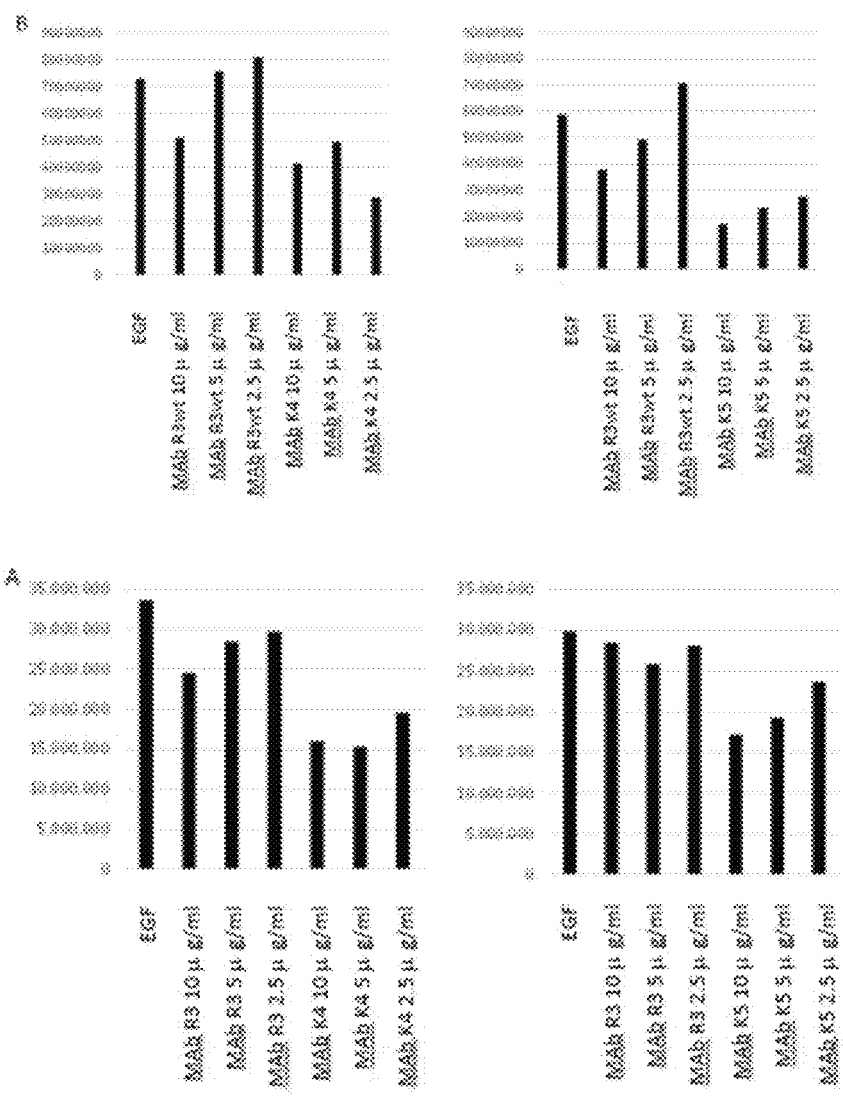
FIG. 7. Inhibition of EGFR phosphorylation mediated by EGF and induced by nimotuzumab and K4 and K5 MAb. (A) Line H125, which has a medium expression of EGFR. (B) MDA-MB-468 line, with high EGFR expression.

The cells were treated for 2 hours with the R3, K4 and K5 mAbs at 10 µg/ml, 5 µg/ml and 2.5 µg/ml. Subsequently, the medium was removed to eliminate the mAbs not bound to the cells, fresh medium with human EGF was added for 10 minutes to induce phosphorylation of the receptor. Next, a lysate was performed in RIPA buffer from these cells exposed to the different treatments. Protein concentration was quantified according to the instructions of the bicinchoninic acid reagent kit (Pierce). 25 µg of proteins from the lysates were applied in a 9% SDS-PAGE gel and the proteins were transferred to a nitrocellulose membrane. The primary Ab produced in rabbit anti-pEGFR (Y1068) was used to detect the phosphorylated EGFR (Phospho-EGFR). The protein content was visualized with the anti-rabbit secondary Ab bound to the HRP fluorophore followed by the chemiluminescent substrate (Pierce). The graphs show the signal obtained with the Phospho-EGFR, which indicates the amount of this protein in the cell lysate. As evidenced in FIG. 7, at all concentrations evaluated, K4 and K5 mAbs showed a greater ability to inhibit EGF-mediated EGFR phosphorylation in both cell lines as compared to nimotuzumab. Furthermore, both mAbs at the lowest concentration evaluated have greater or the same effect as nimotuzumab at the highest concentration evaluated (4 times more concentrated). Although for all mAbs the inhibition is greater in the MDA-MB-468 line, with higher expression of the receptor (FIG. 7B), it is important to highlight that the inhibitory effect of the K4 and K5 mAb is not lost in the cell line with lower expression of the receptor (FIG. 7A) as it occurs with nimotuzumab. The above provides an advantage for the use of these new mAbs obtained from incorporating mutations in the variable region of Nimotuzumab, that result in a greater affinity for its ligand and in a higher biological activity.

The invention claimed is:

1. A recombinant monoclonal antibody (mAb) that recognizes the extracellular region of human epidermal growth factor receptor (Her1), wherein the complimentary determining region (CDR)2 of the variable region of the heavy chains of said mAb are selected from the group consisting of SEQ ID NO. 17 and SEQ ID NO. 18, and wherein the CDR1 and CDR3 sequences of the variable region of the heavy chains of said mAb consist of (SEQ ID NO. 9) and (SEQ ID NO.3), respectively, and wherein the CDR sequences of the variable region of the light chains of said mAb consist of CDR 1 (SEQ ID NO. 22), CDR 2 (SEQ ID NO. 23), and CDR 3 (SEQ ID NO. 24).

2. A recombinant monoclonal antibody (mAb) that recognizes the extracellular region of human epidermal growth factor receptor (Her1), wherein the CDR2 sequence of the variable region of the heavy chains of said mAb is selected from the group consisting of:
SEQ ID NO. 10,
SEQ ID NO. 11,
SEQ ID NO. 12,
and
SEQ ID NO. 29,
wherein the sequence of the variable region of the heavy chain CDR1 is SEQ ID NO. 9 and CDR3 is SEQ ID NO.3, and wherein CDR sequences of the variable region of the light chains of said antibody are CDR 1 (SEQ ID NO. 22), CDR 2 (SEQ ID NO. 23), and CDR 3 (SEQ ID NO. 24).

3. A recombinant monoclonal antibody (mAb) that recognizes the extracellular region of human epidermal growth factor receptor (Her1), wherein the CDR2 sequence of the variable region of the heavy chains of said mAb is SEQ ID NO. 2 or SEQ ID NO. 8, wherein the CDR1 sequence of the variable region of the heavy chains of said mAb is SEQ ID NO. 1 and the CDR3 sequence of the variable region of the heavy chains of said mAb is SEQ ID NO.3, and wherein the CDR1, CDR2, and CDR3 sequences of the variable region of the light chains of said mAb are SEQ ID NO. 22, SEQ ID NO. 23 and SEQ ID NO. 24, respectively.

4. A recombinant monoclonal antibody (mAb) that recognizes the extracellular region of human epidermal growth factor receptor (Her1), wherein the CDR1 sequence of the variable region of the heavy chains of said mAb is SEQ ID NO. 13 or SEQ ID NO. 19, wherein the CDR2 sequence of the variable region of the heavy chains of said mAb is SEQ ID NO. 14 and the CDR3 sequence of the variable region of the heavy chains of said mAb is SEQ ID NO.3, and wherein the CDR1, CDR2, and CDR3 sequences of the variable region of the light chains of said mAb are SEQ ID NO. 22, SEQ ID NO. 23 and SEQ ID NO. 24, respectively.

5. A recombinant monoclonal antibody (mAb) that recognizes the extracellular region of human epidermal growth factor receptor (Her1), wherein the variable region of the heavy chains of said mAb comprises CDR1 (SEQ ID NO. 15), CDR2 (SEQ ID NO. 16) and CDR3 (SEQ ID NO.3), and wherein the variable region of the light chains of said mAb comprise CDR (1 SEQ ID NO. 22), CDR 2 (SEQ ID NO. 23), and CDR 3 (SEQ ID NO. 24).

6. The mAb according to claim 2, wherein the framework regions (FW) of the variable region of the heavy chains of said antibody comprise FW 1 (SEQ ID NO. 4), FW 2 (SEQ ID NO. 5), FW 3 (SEQ ID NO. 6), and FW 4 (SEQ ID NO. 7), and wherein the framework wherein regions (FW) of the variable region of the light chains of said mAb comprise FW 1 (SEQ ID NO. 25), FW 2 (SEQ ID NO. 26), FW 3 (SEQ ID NO. 27), and FW 4 (SEQ ID NO. 28).

7. The mAb according to claim 2, wherein the sequence of said heavy chain constant region is human IgG1.

8. The mAb according to claim 2, wherein the constant region of said light chain is human kappa.

9. An antigen-binding fragment of the mAb according to claim 2, wherein said fragment is a fragment of Fab type.

10. The fragment according claim 9, wherein said fragment is a fragment of (Fab)2 type.

11. A method of treating tumors expressing EGFR in a subject comprising administering a therapeutically effective amount of the mAb according to claim 2 or an antigen-binding fragment thereof to said subject.

* * * * *

SEQUENCE LISTING

```
<160> NUMBER OF SEQ ID NOS: 29

<210> SEQ ID NO 1
<211> LENGTH: 10
<212> TYPE: PRT
<213> ORGANISM: Artificial Sequence
<220> FEATURE:
<223> OTHER INFORMATION: by DNA recombinant technology

<400> SEQUENCE: 1

Gly Tyr Thr Phe Thr Asp Tyr Tyr Ile Tyr
1               5                   10

<210> SEQ ID NO 2
<211> LENGTH: 18
<212> TYPE: PRT
<213> ORGANISM: Artificial Sequence
<220> FEATURE:
<223> OTHER INFORMATION: by DNA recombinant technology

<400> SEQUENCE: 2

Gly Gly Ile Asn Pro Thr Ser Gly Gly Ser Asn Phe Asn Glu Lys Phe
1               5                   10                  15

Lys Thr
```

<210> SEQ ID NO 3
<211> LENGTH: 14
<212> TYPE: PRT
<213> ORGANISM: Artificial Sequence
<220> FEATURE:
<223> OTHER INFORMATION: by DNA recombinant technology

<400> SEQUENCE: 3

Thr Arg Gln Gly Leu Trp Phe Asp Ser Asp Gly Arg Gly Phe
1               5                   10

<210> SEQ ID NO 4
<211> LENGTH: 25
<212> TYPE: PRT
<213> ORGANISM: Artificial Sequence
<220> FEATURE:
<223> OTHER INFORMATION: by DNA recombinant technology

<400> SEQUENCE: 4

Gln Val Gln Leu Gln Gln Ser Gly Ala Glu Val Lys Lys Pro Gly Ser
1               5                   10                  15

Ser Val Lys Val Ser Cys Lys Ala Ser
            20                  25

<210> SEQ ID NO 5
<211> LENGTH: 13
<212> TYPE: PRT
<213> ORGANISM: Artificial Sequence
<220> FEATURE:
<223> OTHER INFORMATION: by DNA recombinant technology

<400> SEQUENCE: 5

Trp Val Arg Gln Ala Pro Gly Gln Gly Leu Glu Trp Ile
1               5                   10

<210> SEQ ID NO 6
<211> LENGTH: 30
<212> TYPE: PRT
<213> ORGANISM: Artificial Sequence
<220> FEATURE:
<223> OTHER INFORMATION: by DNA recombinant technology

<400> SEQUENCE: 6

Arg Val Thr Ile Thr Ala Asp Glu Ser Ser Thr Thr Ala Tyr Met Glu
1               5                   10                  15

Leu Ser Ser Leu Arg Ser Glu Asp Thr Ala Phe Tyr Phe Cys
            20                  25                  30

<210> SEQ ID NO 7
<211> LENGTH: 12
<212> TYPE: PRT
<213> ORGANISM: Artificial Sequence
<220> FEATURE:
<223> OTHER INFORMATION: by DNA recombinant technology

<400> SEQUENCE: 7

Phe Trp Gly Gln Gly Thr Thr Val Thr Val Ser Ser
1               5                   10

<210> SEQ ID NO 8
<211> LENGTH: 18
<212> TYPE: PRT
<213> ORGANISM: Artificial Sequence
<220> FEATURE:
<223> OTHER INFORMATION: DNA recombinant technology -continued

<400> SEQUENCE: 8

Gly Gly Ile Asn Pro Thr Thr Gly Gly Ser Asn Phe Asn Glu Lys Phe
1               5                   10                  15

Lys Thr

<210> SEQ ID NO 9
<211> LENGTH: 10
<212> TYPE: PRT
<213> ORGANISM: Artificial Sequence
<220> FEATURE:
<223> OTHER INFORMATION: by DNA recombinant technology

<400> SEQUENCE: 9

Gly Tyr Thr Phe Thr Asn Tyr Tyr Ile Tyr
1               5                   10

<210> SEQ ID NO 10
<211> LENGTH: 18
<212> TYPE: PRT
<213> ORGANISM: Artificial Sequence
<220> FEATURE:
<223> OTHER INFORMATION: by DNA recombinant technology

<400> SEQUENCE: 10

Gly Gly Ile Asn Pro Thr Thr His Ala Gln Ala Phe Asn Glu Lys Phe
1               5                   10                  15

Lys Thr

<210> SEQ ID NO 11
<211> LENGTH: 18
<212> TYPE: PRT
<213> ORGANISM: Artificial Sequence
<220> FEATURE:
<223> OTHER INFORMATION: by DNA recombinant technology

<400> SEQUENCE: 11

Gly Gly Ile Asn Pro Leu Arg Gly Gln Ala Val Phe Asn Glu Lys Phe
1               5                   10                  15

Lys Thr

<210> SEQ ID NO 12
<211> LENGTH: 18
<212> TYPE: PRT
<213> ORGANISM: Artificial Sequence
<220> FEATURE:
<223> OTHER INFORMATION: by DNA recombinant technology

<400> SEQUENCE: 12

Gly Gly Ile Asn Pro Gln Thr Ser Gln Asn His Phe Asn Glu Lys Phe
1               5                   10                  15

Lys Thr

<210> SEQ ID NO 13
<211> LENGTH: 10
<212> TYPE: PRT
<213> ORGANISM: Artificial Sequence
<220> FEATURE:
<223> OTHER INFORMATION: by DNA recombinant technology

<400> SEQUENCE: 13

Gly Tyr Pro Phe Ser Asn Tyr Tyr Ile Tyr
1               5                   10

```
<210> SEQ ID NO 14
<211> LENGTH: 18
<212> TYPE: PRT
<213> ORGANISM: Artificial Sequence
<220> FEATURE:
<223> OTHER INFORMATION: by DNA recombinant technology

<400> SEQUENCE: 14

Gly Gly Ile Asn Pro Thr Ser Gly Val Ser Asn Phe Asn Glu Lys Phe
1               5                   10                  15
Lys Thr

<210> SEQ ID NO 15
<211> LENGTH: 10
<212> TYPE: PRT
<213> ORGANISM: Artificial Sequence
<220> FEATURE:
<223> OTHER INFORMATION: by DNA recombinant technology

<400> SEQUENCE: 15

Gly Tyr Asn Phe Thr Asp Tyr Tyr Ile Tyr
1               5                   10

<210> SEQ ID NO 16
<211> LENGTH: 18
<212> TYPE: PRT
<213> ORGANISM: Artificial Sequence
<220> FEATURE:
<223> OTHER INFORMATION: by DNA recombinant technology

<400> SEQUENCE: 16

Gly Gly Ile Asn Pro Thr Ser Gly Gly Ser His Phe Asn Glu Lys Phe
1               5                   10                  15
Lys Thr

<210> SEQ ID NO 17
<211> LENGTH: 18
<212> TYPE: PRT
<213> ORGANISM: Artificial Sequence
<220> FEATURE:
<223> OTHER INFORMATION: by DNA recombinant technology

<400> SEQUENCE: 17

Gly Gly Ile Asn Pro Asn Asn Gln Gln Ser His Phe Asn Glu Lys Phe
1               5                   10                  15
Lys Thr

<210> SEQ ID NO 18
<211> LENGTH: 18
<212> TYPE: PRT
<213> ORGANISM: Artificial Sequence
<220> FEATURE:
<223> OTHER INFORMATION: by DNA recombinant technology

<400> SEQUENCE: 18

Gly Gly Ile Asn Pro Val Thr Gln Arg Pro Val Phe Asn Glu Lys Phe
1               5                   10                  15
Lys Thr

<210> SEQ ID NO 19
<211> LENGTH: 10
<212> TYPE: PRT
<213> ORGANISM: Artificial Sequence
<220> FEATURE:
<223> OTHER INFORMATION: by DNA recombinant technology
```

```
<400> SEQUENCE: 19

Gly Tyr Pro Phe Thr Asn Tyr Tyr Ile Tyr
1               5                   10

<210> SEQ ID NO 20
<211> LENGTH: 18
<212> TYPE: PRT
<213> ORGANISM: Artificial Sequence
<220> FEATURE:
<223> OTHER INFORMATION: by DNA recombinant technology

<400> SEQUENCE: 20

Gly Gly Ile Asn Pro Asn Asn Gln Gln Ser His Phe Asn Glu Lys Phe
1               5                   10                  15

Lys Thr

<210> SEQ ID NO 21
<211> LENGTH: 18
<212> TYPE: PRT
<213> ORGANISM: Artificial Sequence
<220> FEATURE:
<223> OTHER INFORMATION: by DNA recombinant technology

<400> SEQUENCE: 21

Gly Gly Ile Asn Pro Val Thr Gln Arg Pro Val Phe Asn Glu Lys Phe
1               5                   10                  15

Lys Thr

<210> SEQ ID NO 22
<211> LENGTH: 16
<212> TYPE: PRT
<213> ORGANISM: Artificial Sequence
<220> FEATURE:
<223> OTHER INFORMATION: by DNA recombinant technology

<400> SEQUENCE: 22

Arg Ser Ser Gln Asn Ile Val His Ser Asn Gly Asn Thr Tyr Leu Asp
1               5                   10                  15

<210> SEQ ID NO 23
<211> LENGTH: 7
<212> TYPE: PRT
<213> ORGANISM: Artificial Sequence
<220> FEATURE:
<223> OTHER INFORMATION: by DNA recombinant technology

<400> SEQUENCE: 23

Lys Val Ser Asn Arg Phe Ser
1               5

<210> SEQ ID NO 24
<211> LENGTH: 9
<212> TYPE: PRT
<213> ORGANISM: Artificial Sequence
<220> FEATURE:
<223> OTHER INFORMATION: by DNA recombinant technology

<400> SEQUENCE: 24

Phe Gln Tyr Ser His Val Pro Trp Thr
1               5

<210> SEQ ID NO 25
<211> LENGTH: 25
<212> TYPE: PRT
```

<213> ORGANISM: Artificial Sequence
<220> FEATURE:
<223> OTHER INFORMATION: by DNA recombinant technology

<400> SEQUENCE: 25

Gln Val Gln Leu Gln Gln Ser Gly Ala Glu Val Lys Lys Pro Gly Ser
1               5                   10                  15

Ser Val Lys Val Ser Cys Lys Ala Ser
            20                  25

<210> SEQ ID NO 26
<211> LENGTH: 13
<212> TYPE: PRT
<213> ORGANISM: Artificial Sequence
<220> FEATURE:
<223> OTHER INFORMATION: by DNA recombinant technology

<400> SEQUENCE: 26

Trp Val Arg Gln Ala Pro Gly Gln Gly Leu Glu Trp Ile
1               5                   10

<210> SEQ ID NO 27
<211> LENGTH: 59
<212> TYPE: PRT
<213> ORGANISM: Artificial Sequence
<220> FEATURE:
<223> OTHER INFORMATION: by DNA recombinant technology

<400> SEQUENCE: 27

Arg Gln Ala Pro Gly Gln Gly Leu Glu Trp Ile Gly Gly Ile Asn Pro
1               5                   10                  15

Thr Ser Gly Gly Ser Asn Phe Asn Glu Lys Phe Lys Thr Arg Val Thr
            20                  25                  30

Ile Thr Ala Asp Glu Ser Ser Thr Thr Ala Tyr Met Glu Leu Ser Ser
        35                  40                  45

Leu Arg Ser Glu Asp Thr Ala Phe Tyr Phe Cys
    50                  55

<210> SEQ ID NO 28
<211> LENGTH: 11
<212> TYPE: PRT
<213> ORGANISM: Artificial Sequence
<220> FEATURE:
<223> OTHER INFORMATION: by DNA recombinant technology

<400> SEQUENCE: 28

Phe Gly Gln Gly Thr Lys Leu Glu Ile Lys Arg
1               5                   10

<210> SEQ ID NO 29
<211> LENGTH: 18
<212> TYPE: PRT
<213> ORGANISM: Artificial Sequence
<220> FEATURE:
<223> OTHER INFORMATION: by DNA recombinant technology

<400> SEQUENCE: 29

Gly Gly Ile Asn Pro Thr Ser Gly Gly Ser Ile Phe Asn Glu Lys Phe
1               5                   10                  15

Lys Thr